(12) United States Patent
Henderson

(10) Patent No.: US 8,372,024 B1
(45) Date of Patent: Feb. 12, 2013

(54) STRETCHABLE BAND FOR LIMB HEMOEVACUATION

(75) Inventor: Eric R. Henderson, Tampa, FL (US)

(73) Assignee: University of South Florida, Tampa, FL (US)

( * ) Notice: Subject to any disclaimer, the term of this patent is extended or adjusted under 35 U.S.C. 154(b) by 234 days.

(21) Appl. No.: 12/842,547

(22) Filed: Jul. 23, 2010

Related U.S. Application Data

(60) Provisional application No. 61/228,393, filed on Jul. 24, 2009.

(51) Int. Cl.
*A61F 5/00* (2006.01)
*A61F 13/00* (2006.01)

(52) U.S. Cl. .......................... 602/75; 602/53

(58) Field of Classification Search ............ 602/75–77, 602/52–53
See application file for complete search history.

(56) References Cited

U.S. PATENT DOCUMENTS

| | | | | |
|---|---|---|---|---|
| 3,613,679 | A * | 10/1971 | Bijou | 602/75 |
| 4,502,301 | A * | 3/1985 | Swallow et al. | 66/178 A |
| 5,195,950 | A * | 3/1993 | Delannoy | 602/75 |
| 5,779,659 | A * | 7/1998 | Allen | 602/75 |
| 6,050,967 | A * | 4/2000 | Walker et al. | 602/75 |
| 6,142,968 | A * | 11/2000 | Pigg et al. | 602/75 |
| 6,338,723 | B1 * | 1/2002 | Carpenter et al. | 602/75 |
| 6,833,001 | B1 | 12/2004 | Chao | |
| 7,422,256 | B2 * | 9/2008 | Mueller | 294/74 |
| 8,267,880 | B2 * | 9/2012 | Ritzdorf et al. | 602/75 |
| 2005/0209545 | A1 * | 9/2005 | Farrow et al. | 602/75 |
| 2007/0219472 | A1 | 9/2007 | Sakura, Jr. | |
| 2010/0312160 | A1 * | 12/2010 | Creighton et al. | 602/62 |

FOREIGN PATENT DOCUMENTS
WO 8301192 A1 4/1983

OTHER PUBLICATIONS

Ishii, Y.; Noguchi, H.; Takeda, M. 2009. "Clinical use of a new tourniquet system for foot and ankle surgery." International Orthopaedics. SpringerLink. http://www.springerlink.com/content/p622q4763334k333/.

Shah, J.S.; Anagnos, D.; Norfleet, E.A. 2002. "Elastic Tourniquet Technique for Decompression of Extremity Compartment Syndrome." Journal of Clinical Anesthesia. 14: 524-528.

McLaren, A.C.; Rorabeck, C.H. 1985. "The pressure distribution under tourniquets." The Journal of Bone & Joint Surgery. 67: 433-438.

Biehl III, W.C.; Morgan, J.M.; Wagner Jr., W.; Gabriel, R.A. 1993. "The Safety of the Esmarch Tourniquet." Foot & Ankle: The official journal of the American Orthopaedic Foot Society. 15-5: 278-283.

(Continued)

*Primary Examiner* — Kim M Lewis
(74) *Attorney, Agent, or Firm* — David F. Jacobs; Ronald E. Smith; Smith & Hopen, P.A.

(57) ABSTRACT

A device for evacuating blood from an extremity includes an elongate stretchable band having a plurality of images printed on a first side of the band. Individual images are arranged in rows and columns along a longitudinal extent of the band. Each image in a first row has a common longitudinal extent and height when the band is in a position of repose. Each image in a second row of images has a common longitudinal extent and height and has a reduced longitudinal extent relative to the images in the first row when the band is in the position of repose. First and second pressure readings are associated with each image in the first and second rows, respectively. The second pressure reading has a higher value than the first, indicating that the images in the second row will expand longitudinally when the second pressure is applied to an extremity.

4 Claims, 3 Drawing Sheets

OTHER PUBLICATIONS

Pauers, R.S.; Carocci, M.A. 1994. "Low Pressure Pneumatic Tourniquets: Effectiveness at Minimum Recommended Inflation Pressures." The Journal of foot and ankle surgery. 33-6: 605-609.

Abraham, E.; Amirouche, F.M.L. 2000. "Pressure Controlled Esmarch Bandage Used as a Tourniquet." Foot & Ankle International. 21-8: 686-689.

* cited by examiner

STRETCHABLE BAND FOR LIMB HEMOEVACUATION

CROSS REFERENCE TO RELATED APPLICATION

This application claims priority to U.S. Provisional Patent Application No. 61/228,393, entitled "Stretchable Band for Limb Hemoevacuation", filed on Jul. 24, 2009, the contents of which are hereby incorporated by reference.

BACKGROUND OF THE INVENTION

1. Field of the Invention

This invention relates, generally, to medical devices. More particularly, it relates to a device that enables accurate application of pressure to a limb being evacuated of blood prior to surgery or for accurate application of pressure to a limb where a stretchable bandage is being applied as a tourniquet.

2. Description of the Prior Art

Tourniquets are commonly used during surgery. Most major surgeries involving an extremity such as knee replacement surgery incorporate a tourniquet in order to minimize blood loss. It is common practice to evacuate blood from an extremity prior to performing surgery involving a tourniquet. This is done by wrapping the extremity using a stretchable band that is continually stretched during the application process so that a circumferential, compressive force is applied to the limb, thereby forcing the blood from the extremity into the rest of the body. While this process forces the venous blood out of the extremity, it also prevents entry of higher pressure arterial blood into the extremity. The wrapping is performed beginning at the distal (furthest from the heart) aspect of the extremity and wrapping proximally toward the body.

Although a certain level of force is required to successfully evacuate blood from each individual patient's extremity prior to activation of the tourniquet (due to limb diameter and the individual patient's blood pressure), the elastic bands used to evacuate extremities do not give any indication of the amount of forces applied to the limb and therefore the surgeon is left to use his or her best judgment as to the efficacy of the band's application. Also, individual wrapping technique could strongly influence the amount of force applied to the limb as an increased degree of overlapping of the band would increase the force on the limb.

SUMMARY OF THE INVENTION

The long-standing but heretofore unfulfilled need for an improved stretchable band is now met by a new, useful, and non-obvious invention.

The novel device for evacuating blood from an extremity includes an elongate stretchable band that is configured into a coil when not in use and that is uncoiled and wrapped around an extremity when in use.

A plurality of images is printed on a first side of the band and includes individual images arranged in rows and columns along a longitudinal extent of the band. A first row of images includes images having a common longitudinal extent and height when the band is in a position of repose. A second row of images includes images having a common longitudinal extent and height and each of the images in the second row has a reduced longitudinal extent relative to the images in the first row when the band is in its unstretched position of repose.

The images in the second row of images are disposed in columnar form with the images in the first row of images.

A first pressure reading is associated with each image in the first row and a second pressure reading is associated with each image in the second row. The second pressure reading has a higher value than the first pressure reading, indicating that the images in the second row will expand in longitudinal extent until their longitudinal extent substantially equals their height when pressure substantially equal to the second pressure reading is applied to an extremity.

In a preferred embodiment, there are five (5) rows of images but the number of rows is not critical. A single row of images would have utility but not as much as a band with more rows. With more rows, a surgeon can more accurately gauge the pressure applied to a limb.

The novel device has rows of markings that indicate the direct pressure of a single wrapping of the device. Rectangles are used as a matter of preference because they are believed to be the easiest to read. The device also has markings that indicate the degree of force increase caused by overlapping of the band when it is applied.

A primary object of this invention is to enable surgeons to more accurately apply stretchable bandages to patients' skin with decreased risk of damage to nerves or skin necrosis.

Other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
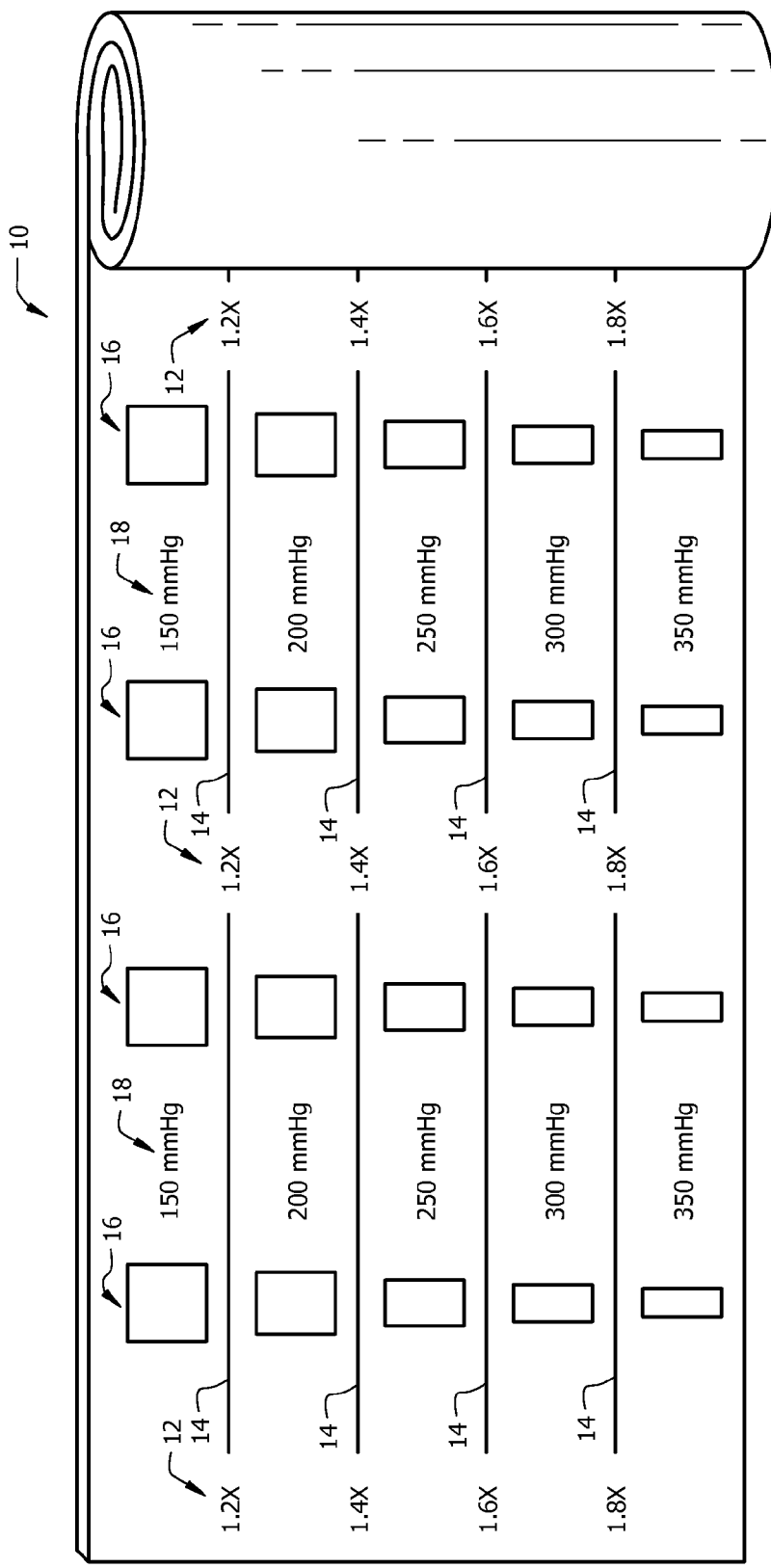
FIG. 1 is a diagrammatic representation of the novel stretchable band.

Referring now to FIG. 1, it will there be seen that a diagrammatic representation of a novel stretchable band is denoted as a whole by the reference numeral 10.

A conventional band used to evacuate blood from extremities for surgical or other purposes is modified by printing images such as rectangles or ellipses on the side of the stretchable band that faces outwards, i.e., away from the patient's skin. The images undergo visually-detectable deformation as the band is stretched. The images are printed in various sizes to indicate approximate amounts of force applied to the band when the images are deformed a certain amount.

In a preferred embodiment, as depicted in FIG. 1, a repeating series of rectangles with differing height-width ratios is printed on the stretchable band so that when the band is stretched to a given length the rectangles corresponding to that pressure deform and become squares. Rectangles with smaller height-width ratios deform sooner and indicate a lower force when a square shape is obtained than rectangles with larger height-width ratios, which deform to a square at higher forces. The rectangles may be color-coded to indicate proper use for specific circumstances, such as pink rectangles for pediatric patients, for example.

Linear bands printed on the wrap indicate the degree of overlap that is occurring, and subsequently how much the force is increased due to overlapping. Numerical indicators of the approximate force multiplier interrupt the lines.

FIG. 1 depicts a length of the stretchable band 10 used to evacuate blood from a limb when said band is in its position of repose, i.e., when it is not stretched. The drawing depicts an unrolled portion of the band facing outward from a patient, i.e., away from the patient's skin so that the markings on the band can be observed.

Several markings are provided on the surface of the band.

From the left side of the paper, the first markings (1.×, 1.4×, etc.), collectively denoted 12, indicate the force multiplier incurred by overlapping the wrap the amount indicated by the linear lines 14 that begin to the right of the first markings 12.

Further to the right, a series of rectangles, collectively denoted 16, decrease in width towards the bottom of the band, i.e., the width decreases from the top row to the bottom row. These rectangles have width-to-height ratios of less than 1.0 and therefore deform to become squares when stretched an appropriate amount. The markings to the right of the squares, collectively denoted 18, indicate the amount of force, in millimeters of mercury, applied to the band (or limb) when the corresponding rectangle is stretched to the point that it resembles a square.

FIG. 1 is an actual-size view of a partially unrolled stretchable band having utility when used to evacuate blood from an extremity. Pressure readings such as "150 mmHg" correspond to the adjacent rectangles and indicate the pressure applied to the limb when the rectangle is stretched to a degree where the short axis or width (in this view the horizontal axis) of the rectangle equals the long axis or height and the rectangle appears to be a square. Multiplier values such as "1.2×" indicate the amount that the pressure applied to the limb is increased when the band is overlapped the amount indicated by the adjacent longitudinal lines.

Figure 2:
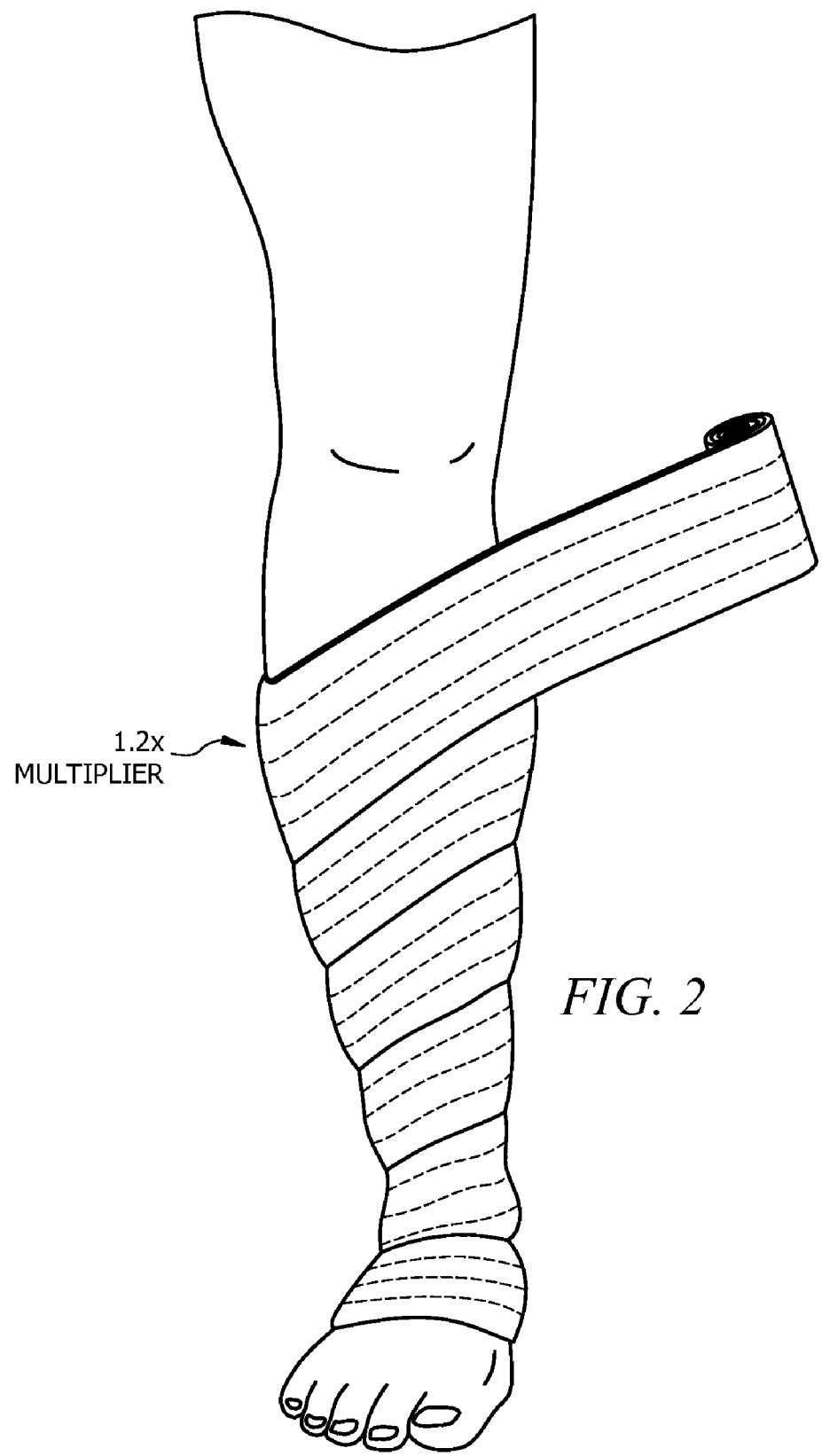
FIG. 2 is a perspective view depicting the novel band when a first amount of overlap is employed when wrapping a limb.
Figure 3:
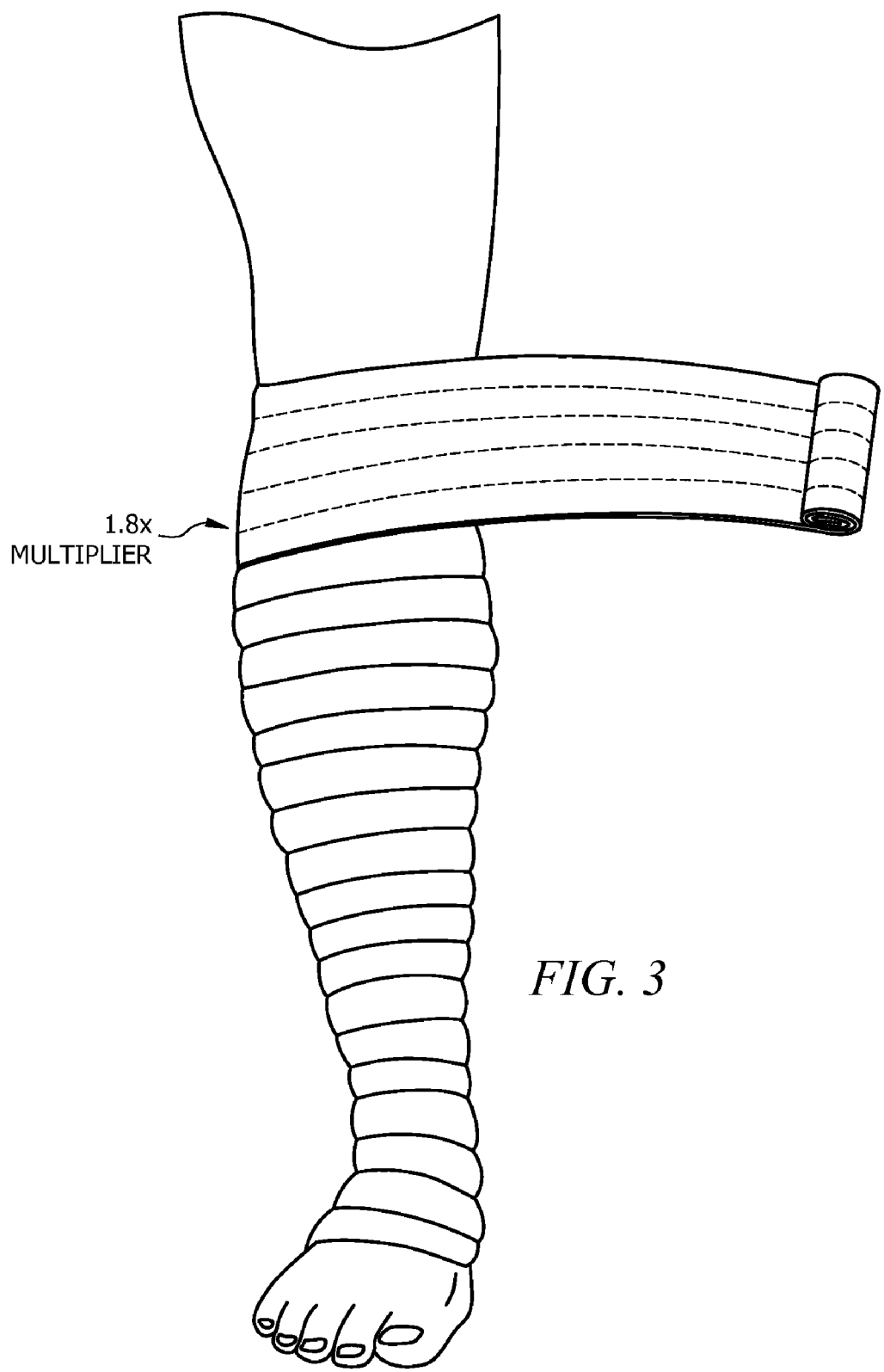
FIG. 3 is a perspective view depicting the novel band when a second amount of overlap greater than said first amount of overlap is employed when wrapping a limb.

FIG. 2 depicts a wrapping where the 1.2 multiplier is used and FIG. 3 depicts a wrapping where a 1.8 multiplier is used. From these two (2) figures, it is apparent that no multiplier is needed when the band is applied with no overlapping, i.e., when contiguous edges abut one another. A small overlap, such as depicted in FIG. 2, thus requires a small multiplier such as 1.2, and so on. From the illustrated examples, it would be easy to draw a 1.0 (no overlap), a 1.4, or a 1.6 overlap.

This invention enables surgeons to more accurately apply stretchable bandages to a patient's limb. To avoid skin sloughing, such bandages are not applied directly to a patient's skin. To decrease the risk of damage to nerves or skin necrosis, a sock or other item made of a thin cloth is usually applied first to avoid applying shear stresses to the skin.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A device for evacuating blood from an extremity, comprising:
   an elongate stretchable band that can be configured into a coil when not in use and that can be uncoiled and wrapped around an extremity in a helical coil when in use;
   a plurality of images printed on a first side of said elongate stretchable band;
   said plurality of images including individual images arranged in rows and columns along a longitudinal extent of said elongate stretchable band;
   said rows separated by linear lines; and
   said linear lines indicating approximate force multiplier incurred from overlapping said band.

2. The device of claim 1, further comprising:
   a first row of images including images having a common longitudinal extent and height when said elongate stretchable band is in a position of repose;
   a second row of images including images having a common longitudinal extent and height and each of said images having a reduced longitudinal extent relative to said images in said first row of images when said elongate stretchable band is in said position of repose.

3. The device of claim 2, further comprising:
   said images in said second row of images being disposed in columnar form with said images in said first row of images.

4. The device of claim 3, further comprising:
   a first pressure reading associated with each image in said first row of images;
   a second pressure reading associated with each image in said second row of images; and
   said second pressure reading having a higher value than said first pressure reading, indicating that said images in said second row of images will expand in longitudinal extent until said longitudinal extent substantially equals said height when pressure substantially equal to said second pressure reading is applied to an extremity.

* * * * *